United States Patent [19]

Storm et al.

[11] Patent Number: 5,576,003

[45] Date of Patent: Nov. 19, 1996

[54] ORNITHOBACTERIUM RHINOTRACHEALE VACCINE AND METHOD OF IMMUNIZATION

[75] Inventors: Paul K. Storm; Paul C. M. van Empel, both of Boxmeer, Netherlands

[73] Assignee: Akzo Nobel N.V., Arnhem, Netherlands

[21] Appl. No.: 244,831

[22] PCT Filed: Oct. 14, 1993

[86] PCT No.: PCT/EP93/02873

§ 371 Date: Jun. 9, 1994

§ 102(e) Date: Jun. 9, 1994

[87] PCT Pub. No.: WO94/09114

PCT Pub. Date: Apr. 28, 1994

[30] Foreign Application Priority Data

Oct. 14, 1992 [EP] European Pat. Off. ............ 92203154

[51] Int. Cl.$^6$ .................. A61K 39/02; C12N 1/12
[52] U.S. Cl. .................. 424/234.1; 424/826; 435/252.1
[58] Field of Search .................. 424/234.1, 826; 435/252.1

[56] References Cited

U.S. PATENT DOCUMENTS 3,534,136 10/1970 Dunlop ........................... 424/89
3,876,763 4/1975 Yoshikazu et al. ............... 424/89
4,379,140 4/1983 Jensen ............................. 424/92

FOREIGN PATENT DOCUMENTS 1036621 7/1966 United Kingdom.

OTHER PUBLICATIONS

Gross, Avian Diseases, 34:607–610 (1990).

Smith et al, J. Gen. Virol, 66:777–786 (1985).

Simmons et al, Avian Diseases 30(4):761–765 (1986).

van den Bosch et al, Inf. & Immun., 61(3):800–806 (Mar. 1993).

Primary Examiner—Irene Marx
Assistant Examiner—S. Saucier
Attorney, Agent, or Firm—William M. Blackstone; Mary E. Gormley

[57] ABSTRACT

The present invention relates to a novel bacterial respiratory poultry disease and the identification of the causative agent *Ornithobacterium rhinotracheale*. A vaccine derived from this agent was effective in preventing the disease in chickens challenged with the virulent field strains.

14 Claims, No Drawings

ORNITHOBACTERIUM RHINOTRACHEALE VACCINE AND METHOD OF IMMUNIZATION

The present invention is concerned with a novel type of gram-negative aerobic rod-shaped bacterium, a vaccine derived thereof and with the use of a novel type of Gram-negative aerobic rod-like bacterium. This bacterium has been classified as a new genus and species, and accorded the name *Ornithobacterium rhinotracheale*.

In the last decades, in many countries a strong rise in both the number of chicken and poultry farms, and in addition, an increasing number of animals per farm has been seen. This situation has a serious consequence: it has caused an increasing need for new and better vaccines and vaccination programmes in these countries. Nowadays, most animals are immunized against a number of diseases of viral, bacterial and parasitic origin. Examples of viral diseases in poultry are Newcastle Disease, Infectious Bronchitis, Turkey Rhinotracheitis, Herpesvirus of Turkeys, Fowlpox, Infectious Bursal Disease, etc. Examples of bacterial diseases are Coryza, Salmonella infections, *Pasteurella multocida* infections and *E. coli* infections.

A new bacterial respiratory disease has surprisingly been observed in chickens and turkeys. The disease was seen in chickens that had been vaccinated against the bacterium *Haemophilus paragallinarum;* the causative agent of a disease called Coryza. Coryza is, as far as known, the only respiratory disease in chicken, caused by bacteria belonging to the families of Pasteurellaceae and Neisseriaceae. The symptoms of this new disease differ from the specific symptoms of Coryza. Coryza is mainly an infection of the upper respiratory tract. Infected animals show a serous to mucoid nasal discharge, facial edema and conjunctivitis. They do however not show the clinical signs belonging to diseases of the lower respiratory tract as e.g. airsacculitis or coughing, pneumonic lungs or pleuritis. Given the fact that the newly discovered disease clearly shows the clinical signs of a lower respiratory tract infection as described below, *H. paragallinarum* could be ruled out as the causative agent.

The newly discovered disease is characterised by the following clinical signs in chickens: The first indication of this new disease is mild snicking. Two or tree days later a small number of broilers usually develop a mild nasal discharge and/or mild facial edema, which disappear after 2–4 days. Snicking continues until the birds are processed. Within 1–3 days from the beginning of respiratory symptoms, evidence of a reduction in feed intake can be detected. This is associated with some increased mortality mainly from broilers succumbing with pneumonic lungs and pleuritis, often with thickened thoracic airsacs. From these lesions, *E. coli* is the dominant isolate. Subsequent losses are mainly associated with extensive airsacculitis. Examination of live broilers at the start of the syndrome usually reveals no specific pathology. From sinuses of affected broilers a pasteurella-like organism can occasionally be isolated. After a couple of days, 30–60 % of the broilers suffer from extensive involvement of especially the abdominal and thoracic airsacs. Especially noticeable is the severe thickening of the airsac membranes. These airsacs often contain a copious amount of a creamy white-yellowish exudate. A somewhat velvety appearance of the airsac is also common. A whitish-creamy foamy exudate is often evident on the mesentery as well. Histopathology reveals a prominent exudative inflammatory process with a fibrinous exudate on the surface and within the membrane, with oedema as well. Accumulation of plasma cells and heterophils are noticeable with some multi-nuclear giant cells and granulomatous infiltrations. No specific micro-organisms are visible in sections with Ziehl-Nielsen and PAS staining. In live birds no pericarditis, perihepatitis or splenitis is usually seen. From affected airsacs Pasteurella/Neisseria-like organisms were isolated. These isolates did not seem to be classic species in the sense that they do in spite of their relatedness to Pasteurella and Neisseria, not belong to these species and some variation in their biochemical abilities has been noticed.

In turkey flocks in several parts of the world, a comparable infection of the upper respiratory tract was found. At first appearance, a low mortality wax found, although at this moment mortality in flocks suffering from the disease can be as high as 5%. The first clinical signs are comparable to infection in chicken: sneezing and nasal discharge. In some animals clinical signs of acute infection were seen. Examination of sacrificed animals showed edema of the lungs, fibrinopurulent pneumonia and often serofibrinous pericarditis and serofibrinous infection of the airsacs.

Bacteria were isolated from infected airsacs and purified. After purification, isolates were grown on rich agar dishes in order to obtain large quantities of pure pathogen. In order to check for the validity of the Koch postulates, a group of S(pecific) P(athogen) F(ree) animals was infected with a mixture of isolates. After infection, they all showed clinical signs that were indistinguishable from those, seen in field infections. From the airsacs of these infected animals, bacteria were isolated that were serologically indistinguishable from the challenge strains.

Four similar highly homologous strains were isolated from the airsacs of sick chickens. One very similar strain was isolated from the airsacs of turkeys. The strains were identified as being Gram-negative aerobic rods. The various isolates show minor differences in their respective fermentation-patterns. All strains however clearly belong to the same serotype, i.e. serum raised against each of the five strains (cross-)reacted with each of the strains. One of the chicken-strains is deposited at the Centraalbureau voor Schimmelcultures (CBS), Oosterstraat 1, PO.box 273, 3740 AG Baarn, The Netherlands, under accession-number 400.92.

The invention provides a novel type of gram-negative aerobic rod-shaped bacterium, said novel type of bacterium being characterised by the bacterium deposited at the Centraalbureau voor Schimmelcultures under deposit number 400.92 the date of deposit being Sep. 8, 1992.

With the wording "bacteria of a novel type" is meant gram-negative aerobic rod-shaped bacteria that are serologically related to the deposited strain. Serologically related bacteria are bacteria that display cross-reactivity with sera raised against the deposited strain.

In particular, gram-negative aerobic rod-shaped bacteria are envisaged that give a higher titer, in serological tests, with antiserum against the deposited strain than with antisera against known gram-negative aerobic rod-shaped bacteria.

More in particular, the present invention is directed to gram-negative aerobic rod-shaped bacteria that positively react in an Agar Gel Precipitation test with antiserum derived against the deposited strain.

The deposited bacterium was typed according to standard determination methods, using Bergey's Manual of Systematic Bacteriology Volume 1 (1984, Williams and Wilkins, 428 East Preston Street, Baltimore U.S.A., 1984) and A.P.I SYSTEM, La Balme-les-Grottes 38390 Montalieu-Vercie, France, system numbers API 20E, API 20NE, API 50CHE, API ZYM, API OF. Results are shown in table 1.

TABLE 1

| differentiation tests. | |
|---|---|
| nitrate reduction | − |
| V-factor requirement | − |
| catalase | − |
| cytochrome-oxidase | + |
| growth on McConkey-agar | − |
| Voges Proskauertest (37° C.) | + (weakly) |
| Urease | + |
| lysine decarboxylase | − |
| ornithine decarboxylase | − |
| O.N.P.G. or P.N.P.G. (β-gal) | + |
| strictly aerobic | − |
| arginine dehydrolase | + (temp.-dependent) |
| indole | − |
| fermentation of: | |
| fructose | + |
| lactose | + |
| galactose | + |

The combination of characteristic properties as given in table 1 makes the novel type of bacteria unique compared to other known bacterial poultry pathogens. (Diseases of Poultry 8, Iowa State University Press 1984). Incidentally, a strain according to the invention may react negatively in a test of table 1, where the deposited strain reacts positively, or vice versa. This is especially the case when the reaction is varying between weakly positive and negative. This may be due to small differences between the tested strains; slight differences are inherent to biological systems. It may also be due to small differences in the reaction conditions in various test-labs.

Several chicken strains with the characteristics of the deposited bacterium have been isolated from chickens suffering from the disease described above, and antisera induced after challenge with live pathogens in Specific Pathogen Free chickens have been checked for (cross-)reaction with the isolated strains. As is shown in table 2, antiserum raised against each strain as determined by an ELISA-method using boiled capsular antigen according to the method of Heddleston, K. L. et al. (Avian Diseases 16:925 (1972)) gives a positive reaction i.e. >6 with all other strains.

TABLE 2

(cross-)reactivity of the deposited strain and three homologous strains, determined by ELISA.

| | titer against strain | | | |
|---|---|---|---|---|
| Challenge | 3037/91 | 3263/91 | 3290/91/(A) | 3290/91/(K) |
| 3037/91 | 7 | 7 | 8 | 7 |
| 3263/91 | 13 | 12 | >13 | 13 |
| 3290/91(A) | 9 | 9 | 11 | 10 |
| 3290/91(K) | 13 | 12 | 12 | 12 |

The underlined strain is of the bacterium, deposited under nr. CBS 400.92

Pooled sera of groups of broilers, vaccinated with one of the strains given in the table, (vaccines prepared as in Example I), were tested in the ELISA test described above for (cross-)reactivity. Titers were raised after repeated vaccination in the presence of adjuvant. Strain GGD 1261 is a strain, recently isolated from turkeys by Dr H. M. Hafez, State Veterinary Laboratory of Stuttgart Germany). As is clearly shown in table 3, all strains are (cross-)reactive, although strains originating from chickens react better with antisera against chicken strains, and the turkey-strain react better with antisera against the turkey strain.

TABLE 3 serological responses, after vaccination, of the combined sera of the groups against boiled capsular extracts. Serum taken 3 weeks after 2$^{nd}$ vaccination.

| | | boiled capsular extracts prepared from: | | | | |
|---|---|---|---|---|---|---|
| Serum nr. | vacc. with | 3037/91 | 3263/91 | 3290/91(A) | 3290/91(K) | GGD-1261 |
| 612 | CONTROL | <6 | 7 | <6 | <6 | <6 |
| 613 | 3037/91 | >19 | >19 | >19 | >19 | 11 |
| 614 | 3263/91 | >19 | >19 | >19 | >19 | 17 |
| 615 | 3290/91(A) | 19 | 19 | 19 | >19 | 13 |
| 616 | 3290/91(K) | 19 | 19 | 19 | >19 | 14 |
| 619 | GGD-1261 | 10 | 11 | 11 | 12 | >19 |

The underlined strain is of the bacterium deposited under nr. CBS 400-92

It is obvious, that any strain isolatable from airsacs of animals suffering from the described illness and serologically related to the deposit strain also falls within the scope of the present invention. Thus, the novel type of bacterium comprises bacteria which are cross-reactive with the deposited bacterial strain, i.e. serum raised against a novel type bacterium binds to the deposited bacterium and vice versa.
In order to discriminate between the novel type of bacterium of the present invention and other gram-negative aerobic rod-shaped bacteria, two serological tests were done:
a) the strain of the present invention was tested in an Agar Gel Precipitation test according to Heddlestone (Heddleston, K. L. et al. (Avian Diseases 16:925 (1972)) against strain 3037/91, strain 3290/91(A), strain 3290/91(K), all isolated from chickens, and strain GGD1261, isolated from turkey. In all cases, cross-reaction was found. The strain of the present invention was also tested with *Haemophilus paragallinarum* strains H18, Spross, 0083, against *Kingella kingae*, and *Kingella denitrificans*, against *Suttonella indologenes*, against *Pasteurella galli-* narum, against the known 16 serotypes of *Pasteurella multocida* and against 10 serotypes of *Pasteurella anatipestifer*. No cross-reactivity was found.

b) The strains mentioned in Table 3 were tested in an ELISA assay against three different serotypes of *Haemophilus paragallinarum*, against two Kingella strains, against *Suttonella indologenes* and against *Pasteurella gallinarum*. The results, given in table 4 show that, although the cross-reactivity between related strains is (very) high, there is no cross-reactivity between any of the strains from table 3 and the known strains listed in table 4.

The invention also relates to a microbiological culture comprising a bacterium of the novel type as described above. The culture may be made by growing said bacteria at a temperature of between 30° and 41° C. The bacteria may be grown under normal atmospheric oxygen pressure whereas the percentage of $CO_2$ in the environment is preferentially kept between 0% and 10%. The bacteria can be grown in a variety of different general purpose bacterial growth promoting media e.g. Luria Broth or Brain Heart Infusion broth. The bacteria may also be grown on eggs, e.g.

TABLE 4a

SEROLOGICAL RESPONSES OF THE COMBINED SERA OF THE GROUPS AGAINST BOILED CAPSULAR EXTRACTS SERUM TAKEN 3 WEEKS AFTER 2nd VACCINATION.
Sera with a titer of 10 or >10 are considered to belong to to the same serotype.

| SERUM NR | VACC. WITH | TITRE (IN 2 LOG) AGAINST B.C.A. OF STRAIN; | | | | |
|---|---|---|---|---|---|---|
| | | 3037/91 | 3263/91 | 3290/91(A) | 3290/91(K) | GGD-1261 |
| 612 | control | <6 | 7 | <6 | <6 | <6 |
| 613 | 3037/91 | >19 | >19 | >19 | >19 | 11 |
| 614 | 3263/91 | >19 | >19 | >19 | >19 | 17 |
| 615 | 3290/91(A) | 19 | 19 | 19 | >19 | 13 |
| 618 | 3290/91(K) | 19 | 19 | 19 | >19 | 14 |
| 619 | GGD-1261 | 10 | 11 | 11 | 12 | >19 |
| 620 | Hpg-H18 | 8 | 9 | 8 | 8 | 8 |
| 621 | Hpg-Spross | 7 | 8 | 8 | 8 | 8 |
| 622 | Hpg-0083 | 7 | 8 | 8 | 8 | 7 |
| 628 | K. kingae | 7 | 8 | 8 | 7 | 7 |
| 629 | K. denitr. | 7 | 9 | 8 | 9 | 7 |
| 630 | S. indolog. | 6 | 7 | 8 | 7 | 6 |
| 631 | P. gallin. | 6 | 8 | 7 | 7 | 6 |

TABLE 4b

SEROLOGICAL RESPONSES OF THE COMBINED SERA OF THE GROUPS AGAINST BOILED CAPSULAR EXTRACTS SERUM TAKEN 3 WEEKS AFTER 2nd VACCINATION.
Sera with a titer of 10 or >10 are considered to belong to to the same serotype.

| SERUM NR | VACC. WITH | TITRE (IN 2 LOG) AGAINST B.C.A. OF STRAIN; | | | | | | |
|---|---|---|---|---|---|---|---|---|
| | | Hpg-H18 | Hpg-SPROSS | Hpg-0083 | K. kingae | K. denitr. | S. indolog. | P. gallin. |
| 612 | control | <6 | <6 | <8 | <6 | 8 | 6 | <6 |
| 613 | 3037/91 | 7 | 6 | 6 | <9 | <9 | <9 | 6 |
| 614 | 3263/91 | <6 | 6 | <6 | <9 | <9 | <9 | 6 |
| 615 | 3290/91(A) | 7 | 8 | 7 | <9 | <9 | <9 | 7 |
| 618 | 3290/91(K) | 6 | 8 | 6 | <9 | <9 | <9 | 7 |
| 619 | GGD-1261 | 6 | 7 | 6 | <6 | 7 | 7 | 7 |
| 620 | Hpg-H18 | >13 | 13 | 10 | 8 | 12 | 11 | 9 |
| 621 | Hpg-Spross | 11 | >13 | >13 | 8 | 12 | 11 | 9 |
| 622 | Hpg-0083 | 11 | 13 | >13 | 9 | 11 | 11 | 8 |
| 628 | K. kingae | 8 | 9 | 7 | >15 | 15 | 7 | 7 |
| 629 | K. denitr. | 9 | 9 | 7 | 12 | >15 | 7 | 7 |
| 630 | S. indolog. | 6 | 6 | <6 | 6 | 6 | >15 | 6 |
| 631 | P. gallin. | 8 | 9 | 8 | 8 | 8 | 8 | >13 |

Preferably, the invention provides bacteria of a novel type as defined above, further characterised in that they display the biochemical properties given in table 1.

In particular, the present invention provides a specific strain of the novel bacterium, i.e. the strain deposited at the Centraalbureau voor Schimmelcultures (CBS), Oosterstraat 1, PO.box 273, 3740 AG Baarn, The Netherlands, under accession-number 400.92.

embryonated chicken or turkey eggs. These eggs may be incubated preferentially between 35° and 40° C.

The invention further provides a vaccine derived from the newly identified bacteria defined above.

Preferably, the invention provides a vaccine comprising bacteria derived from the strain deposited with the CBS under nr. 400.92.

The vaccine according to the invention may comprise the bacteria in live or attenuated live or inactivated form.

Furthermore, fractions of whole cells may also be used as the relevant immunogen in the vaccine according to the invention.

In a preferred embodiment, said vaccine comprises inactivated bacteria. Various physical and chemical methods of inactivation are known in the art. Examples of physical inactivation are UV-radiation, X-ray radiation, gamma-radiation and heating. Examples of inactivating chemicals are β-propiolactone, glutaraldehyde, ethyleneimine and formaldehyde.

Preferably the strain is inactivated with formaldehyde. It is obvious that other ways of inactivating the bacteria are also embodied in the present invention.

The vaccine according to the invention in a preferred presentation also comprises an adjuvant. Adjuvants in general comprise substances that boost the immune response of the injected animal. A number of different adjuvants are known in the art. Examples of adjuvants are Freunds Complete and Incomplete adjuvant, vitamin E, non-ionic block polymers, muramyldipeptides, Quill A, mineral oil, vegetable oil, and Carbopol (a homopolymer). In addition, the vaccine may comprise one or more suitable emulsifiers, e.g. Span or Tween.

In a preferred embodiment, the bacterin comprises a water-in-oil emulsion adjuvant. It goes without saying, that other ways of adjuvating the bacteria are also embodied in the present invention.

The vaccine in the present invention contains at least one antigen of a bacterium of the novel type characterised by the bacterium deposited under CBS 400.92. This includes whole cells, bacterial extracts, Outer Membrane Fractions, bacterial exo- and/or endotoxins, and purified proteins. It is obvious that antigenic polypeptides or fragments thereof may for example be obtained from purified bacterial proteins or by expression of the corresponding genetic material in some pro- or eu-karyotic expression-system or by organo-chemical synthesis.

The vaccine in the present invention may in addition to antigens of the novel bacteria also contain antigenic material of at least one of the viruses and/or microorganisms of the group of poultry-pathogens, preferably in the form of live or inactivated viruses or microorganisms.

In a more preferred embodiment, said vaccine also comprises antigenic material of the viruses or bacteria selected from, but not restricted to, the group consisting of Infectious Bronchitisvirus, Newcastle Diseasevirus, Infectious Bursal Diseasevirus (Gumboro), Chicken Anaemia agent, Avian Reovirus, Mycoplasma gallisepticum, Turkey Rhinotracheitisvirus, *Haemophilus paragallinarum* (Coryza), Chicken Poxvirus, Avian Encephalomyelitisvirus, Fowl Cholera and *E. coli*.

The present invention also relates to the use of bacteria of the novel type for the preparation of a vaccine for the prevention of respiratory diseases.

EXAMPLE I

Growth of the novel bacteria, preparation of the vaccine and vaccination of broilers Cells of the highly identical isolates strain 3037/91, 3263/91 (deposited strain CBS 400.92), 3290/91(A) and 3290/91(K) were grown on sheepblood-agar for 48 hours at 37° C. with the use of a Gas-pac system in order to obtain a 5–10% $CO_2$ environment. Cells were washed off and a C(olony) F(orming) U(nits) count was performed. Cells were killed by adding formaldehyde to a final concentration of 0.185%. After a sterility-check, cells were diluted to $5*10^8$ C.F.U./cell-type in 1 ml of the final vaccine.

The vaccine was prepared by mixing the four strains and oil-adjuvant (a water-in-oil emulsion on the basis of a mineral oil with a ratio of 55% oil/45% water) to a final concentration of $5*10^8$ cells/strain/ml.

Vaccination was done in broilers at ten days of age and was performed by injection of 0.5 ml of the vaccine subcutaneously halfway the neck.

EXAMPLE II

Preparation of challenge strains and challenge of vaccinated and control groups

Preparation 1): bacterial strains 3037/91, 3263/91, 3290/91(A) and 3290/91(K) were grown in Brain Heart Infusion broth, for 20 hrs at 37° C. For challenge, preparations were made that contain the following number of cells in the final challenge-volume:

$3.4*10^8$ c.f.u. of strain 3037/91

$2.2*10^8$ c.f.u. of strain 3263/91

$3.4*10^8$ c.f.u. of strain 3290/91(A)

$7.0*10^7$ c.f.u. of strain 3290/91(K)

Preparation 2): embryonated eggs were inoculated with bacterial strains 3037/91, 3263/91, 3290/91(A) and 3290/91(K). The eggs were incubated at 37° C. and egg-yolk was harvested after 2 days. For challenge, preparations were made that contain the following number of cells in the final challenge-volume:

$3.6*10^6$ c.f.u. of strain 3037/91

$6.6*10^7$ c.f.u. of strain 3263/91

$4.6*10^7$ c.f.u. of strain 3290/91(A)

$4.4*10^7$ c.f.u. of strain 3290/91(K)

At 32 days of age, 9 vaccinated and 9 non-vaccinated animals were challenged into the right thoracic airsac with 0.2 ml of the challenge-mixture, mentioned above as preparation 1. At 41 days of age, the animals were weighed and a post mortem was performed At 35 days of age, 9 vaccinated and 8 non-vaccinated animals were challenged into the right thoracic airsac with 0.2 ml of the challenge- mixture, mentioned above as preparation 2. At 41 days of age, the animals were weighed and a post mortem was done.

Results

A) Virulence of strain 3263/91 in chickens

The table 5 given below shows the virulence of strain 3263/91 deposited under CBS 400.92 in broilers, determined by growth-retardation, when it is used as a live challenge-strain. Growth retardation is a result of the disease, and as such is a good indicator for the virulence of pathogenic strains, and also for the efficacy of vaccination. The strain was grown on egg-yolk as described under EXAMPLE II: preparation of challenge strains. Challenge material was brought directly into the airsacs, in a concentration of $1.2*10^8$ C.F.U. per animal.

TABLE 5

Comparison of growth-development in chickens infected with live strain 3262/91 and control group.

| Challenge | strain 3263/91 | control group |
|---|---|---|
| Average weight day 0 | 1100 (± 98) | 1143 (± 110) |
| Average weight day 8 | 1179 (± 132) | 1478 (± 92) |
| Average weight day 14 | 1684 (± 162) | 1935 (± 91) |
| Average weight diff. day 0–8 | 93 (± 114)[a] | 314 (± 64) |
| Average weight diff. day 0–14 | 600 (± 165)[b] | 796 (± 74) |

[a]significantly different from the control group, $p < 0.005$
[b]significantly different from the control group, $p < 0.05$

B) Virulence of strain 3263/91 and GGD 1261 in turkeys

The table 6 given below shows the virulence of strain 3263/91 deposited under CBS 400.92 and the turkey strain GGD 1261 in turkeys, determined by growth-retardation, when they are used as live challenge-strains. The strains were grown on egg-yolk as described under EXAMPLE II: preparation of challenge strains. Challenge material was brought directly into the airsacs, in a concentration of $5*10^8$ C.F.U. per animal at an age of 32 days. Eleven days after the infection, the turkeys were sacrificed.

TABLE 6

Comparison of growth-development in turkeys infected with live strain 3262/91, live strain GGD 1261 and control group.

| Challenge | strain 3263/91 | strain GGD | control group |
|---|---|---|---|
| Average daily Weight gain after 11 days (grams) | 65[a] | 56[b] | 82 |

[a]significantly different from the control group, $p < 0.001$
[b]significantly different from the control group, $p < 0.001$ c) Vaccination-challenge experiments in relation with pathology

1) The non-vaccinated group of 9 birds, challenged with the mixture of B.H.I.-cultures showed swollen heads or swollen wattles in 5 out of 9 animals, while the airsacs of 7 of the birds showed minor yellowish spots restricted to only the injection-site. The vaccinated group of 9 birds, challenged with the mixture of B.H.I.-. cultures showed swollen heads or swollen wattles only in 2 out of 9 birds, while the airsac of all the birds was fully clear, and showed no spots at the injection site.

2) The control group of 9 birds, challenged with the mixture of egg-yolk cultures showed minor yellowish spots at the injection site in 3 out of 8 birds. In 3 birds some turbidity of the airsacs was seen, while one bird had a creamy exudate in all airsacs. From this exudate, a pure culture of bacteria fully homologous to the deposited strain could be grown. Only one bird showed no reaction at all. The vaccinated group of nine birds, challenged with the mixture of egg-yolk cultures showed healthy birds with very clear airsacs without spots at the injection-site.

D) Vaccination-challenge experiments in relation with daily weight-gain

In table 7, the average daily weight gain of chickens over a period of 34 days is given. It is easily seen from this table on the basis of differences in daily weight gain, that turkey strain GGD 1261 is pathogenic for chickens. Most important however is the notice, that vaccination with the deposited strain 3263/91 gives protection against GGD-1261 challenge.

TABLE 7 vaccination challenge experiments in chickens with vaccines based on strain 3263/91 and GGD 1261

| GROUP | AVG | STD | n |
|---|---|---|---|
| control | 60 | 14 | 10 |
| chall GGD-1261 | 42 | 9 | 10 |
| vacc. GGD-1261 and hom. chall. | 61 | 24 | 10 |
| vacc 3263/91 + chall GGD-1261 | 60 | 12 | 10 |

| GROUPS | P = |
|---|---|
| Group 1 vs Group 2 | <0.005 |
| Group 1 vs Group 3 | >0.05 |
| Group 2 vs Group 3 | <0.025 |
| Group 2 vs Group 4 | <0.005 |

AVG = average, STD = standard deviation, n = number of animals.

In conclusion, the results show, that strain 3263/91, deposited under CBS 400.92 is in its live form a virulent challenge-strain, capable of inducing growth-retardation, swollen wattles, swollen heads and airsacculitis. When used in a vaccine-preparation, inactivated cells of the novel bacteria are capable of inducing protection against clinical symptoms, caused by live strains in both chickens and turkeys.

We claim:

1. A vaccine effective against a disease of the lower respiratory tract in poultry, comprising inactivated *Ornithobacterium rhinotracheale*.

2. The vaccine according to claim 1, wherein the vaccine also comprises an adjuvant.

3. The vaccine according to claim 2, further comprising at least one other antigen from a virus or microorganism pathogenic to poultry.

4. The vaccine according to claim 3, wherein the microorganism or virus is selected from the group consisting of Infectious Bronchitis Virus, Newcastle Disease Virus, Infectious Bursal Disease, Chicken Anemia agent, Avian Reovirus, *Mycoplasma gallisepticum*, Turkey Rhinotracheitis Virus, *Haemophilus paragallinarum*, Chicken Poxvirus, Avian Encephalomyelitis Virus, Fowl Cholera and *E. coli*.

5. The vaccine according to claim 1, wherein it further comprises at least one other antigen from a virus or microorganism pathogenic to poultry.

6. A vaccine according to claim 5, wherein the microorganism or virus is selected from the group consisting of Infectious Bronchitis Virus, Newcastle Disease Virus, Infectious Bursal Disease, Chicken Anemia agent, Avian Reovirus, *Mycoplasma gallisepticum*, Turkey Rhinotracheitis Virus, *Haemophilus paragallinarum*, Chicken Poxvirus, Avian Encephalomyelitis Virus, Fowl Cholera and *E. coli*.

7. The vaccine according to claim 1, wherein the *Ornithobacterium rhinotracheale* is that which is deposited at the Centraalbureau vor Schimmecultures (CBS) under Deposit No. 400.92.

8. The vaccine according to claim 7, wherein the vaccine also comprises an adjuvant.

9. The vaccine according to claim 8, further comprising at least one other antigen from a virus or microorganism pathogenic to poultry.

10. The vaccine according to claim 9, wherein the microorganism or virus is selected from the group consisting of Infectious Bronchitis Virus, Newcastle Disease Virus, Infectious Bursal Disease, Chicken Anemia agent, Arian Reovirus, *Mycoplasma gallisepticum,* Turkey Rhinotracheitis virus, *Haemophilus paragallinarum,* Chicken Poxvirus, Avian Encephalomyelitis Virus, Fowl Cholera and *E. coli.*

11. The vaccine according to claim 7, which further comprises at least one other antigen from a virus or microorganism pathogenic to poultry.

12. A vaccine according to claim 11, wherein the microorganism or virus is selected from the group consisting of Infectious Bronchitis virus, Newcastle Disease Virus, Infectious Bursal Disease, Chicken Anemia agent, Arian Reovirus, *Mycoplasma gallisepticum,* Turkey Rhinotracheitis Virus, *Haemophilus paragallinarum,* Chicken Poxvirus, Avian Encephalomyelitis Virus, Fowl Cholera and *E. coli.*

13. A method of immunizing poultry against bacterial respiratory disease, comprising administering an immunologically effective amount of a vaccine according to claim 1.

14. A method of immunizing poultry against bacterial respiratory disease, comprising administering an immunologically effective amount of a vaccine according to claim 7.

* * * * *